United States Patent
Miller

(10) Patent No.: US 10,441,393 B2
(45) Date of Patent: Oct. 15, 2019

(54) RESONANTLY DRIVEN POWER TOOTHBRUSH HAVING A PRESSURE-SENSING CAPABILITY USING A HALL EFFECT SENSOR

(71) Applicant: KONINKLIJKE PHILIPS N.V., Eindhoven (NL)

(72) Inventor: Kevin Arnold Miller, Bellevue, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 628 days.

(21) Appl. No.: 14/425,338

(22) PCT Filed: Aug. 30, 2013

(86) PCT No.: PCT/IB2013/058139
§ 371 (c)(1),
(2) Date: Mar. 3, 2015

(87) PCT Pub. No.: WO2014/037856
PCT Pub. Date: Mar. 13, 2014

(65) Prior Publication Data
US 2015/0230898 A1   Aug. 20, 2015

Related U.S. Application Data

(60) Provisional application No. 61/698,078, filed on Sep. 7, 2012.

(51) Int. Cl.
*A61C 17/00* (2006.01)
*A61C 17/22* (2006.01)
(Continued)

(52) U.S. Cl.
CPC ........ *A61C 17/221* (2013.01); *A46B 15/0012* (2013.01); *A46B 15/0038* (2013.01);
(Continued)

(58) Field of Classification Search
CPC ....... A61C 17/221; A61C 17/34; A61C 17/22; A61C 17/32; A61C 17/3409;
(Continued)

(56) References Cited

U.S. PATENT DOCUMENTS

| | | |
|---|---|---|
| 5,784,742 A | 7/1998 | Giuliani et al. |
| 5,894,620 A | 4/1999 | Polaert et al. |

(Continued)

FOREIGN PATENT DOCUMENTS

| | | | | |
|---|---|---|---|---|
| CN | 101730512 A | * | 6/2010 | ............. A61C 17/32 |
| EP | 1228737 A2 | * | 8/2002 | ............ A61C 1/0015 |

(Continued)

OTHER PUBLICATIONS

Wetterlin, "A Method of Using Quadrature Sampling to Measure Phase and Magnitude", Jun. 1, 2007, pp. 1-8.

(Continued)

*Primary Examiner* — Monica S Carter
*Assistant Examiner* — Katina N. Henson

(57) ABSTRACT

The toothbrush includes a handle portion which includes a power drive system (14) and further includes a brushhead assembly (20), which includes a brushhead arm having a brush element (21) at a distal end thereof A drive train assembly (12) is responsive to a drive signal from the power assembly for converting the action of the power assembly to a motion of the brushhead assembly. A magnet (30) is secured to the rear of the drive train, with a Hall effect sensor (32) mounted within the magnetic field produced by the magnet as the toothbrush moves in operation. Pressure on the brush element produces a phase shift of the Hall sensor output. A processor (15) determines the value of the phase shift of the Hall sensor signal as pressure is applied to the brush member and produces a signal indicative of the (Continued)

pressure applied by using stored information (71) which relates phase shift to pressure for the particular appliance.

10 Claims, 5 Drawing Sheets

(51) Int. Cl.
*A46B 15/00* (2006.01)
*A61C 17/34* (2006.01)
*A46B 13/02* (2006.01)
*A61C 17/32* (2006.01)

(52) U.S. Cl.
CPC .............. *A61C 17/34* (2013.01); *A46B 13/02* (2013.01); *A46B 13/023* (2013.01); *A46B 15/0002* (2013.01); *A46B 15/0004* (2013.01); *A61C 17/22* (2013.01); *A61C 17/32* (2013.01); *A61C 17/3409* (2013.01); *A61C 17/3481* (2013.01)

(58) Field of Classification Search
CPC ............ A61C 17/3481; A46B 15/0012; A46B 15/0038; A46B 13/02; A46B 13/023; A46B 15/0002; A46B 15/0004
USPC ................................. 15/22.1, 28, 22, 23, 22.4
See application file for complete search history.

(56) References Cited

U.S. PATENT DOCUMENTS

| | | | |
|---|---|---|---|
| 8,397,332 B2 | 3/2013 | Kraus et al. | |
| 8,544,131 B2* | 10/2013 | Braun | A46B 15/0002 15/105 |
| 2009/0241276 A1* | 10/2009 | Hall | A61C 17/221 15/22.1 |
| 2010/0162500 A1 | 7/2010 | Hilscher et al. | |
| 2012/0151698 A1* | 6/2012 | Schaefer | A61C 17/222 15/28 |

FOREIGN PATENT DOCUMENTS

| | | |
|---|---|---|
| GB | 2097663 A | 11/1982 |
| JP | H07116027 A | 5/1995 |
| WO | 2010151582 A1 | 12/2010 |

OTHER PUBLICATIONS

Benavides, "Efficient Fixed-Point Trigonometry Using Cordic Functions for PIC16F", Microchip, AN1061, 2007, pp. 1-12.

Langeveld et al: "Product Sound Design: Intentional and Consequential Sounds" Chapter 3 of "Technology" Advances in Industrial Design Engineering, Edited by Denis A. Coelho, ISBN 978-953-51/1016-3, Published March 2013.

* cited by examiner

RESONANTLY DRIVEN POWER TOOTHBRUSH HAVING A PRESSURE-SENSING CAPABILITY USING A HALL EFFECT SENSOR

CROSS-REFERENCE TO PRIOR APPLICATIONS

This application is the U.S. National Phase application under 35 U.S.C. § 371 of International Application No. PCT/IB2013/058139, filed on Aug. 30, 2013, which claims the benefit of U.S. Provisional Patent Application No. 61/698,078, filed on Sep. 7, 2012. These applications are hereby incorporated by reference herein.

TECHNICAL FIELD

This invention relates generally to resonant driven power toothbrushes, and more specifically concerns such a toothbrush which includes a pressure-sensing mechanism.

BACKGROUND OF THE INVENTION

The use of a pressure-sensing mechanism in toothbrushes, both power and manual, is generally well known, and has been implemented in a variety of specific embodiments. Pressure sensors detect the force applied to the bristle field of the toothbrush. Such sensors can comprise, for example, a simple spring, a moment arm and a switch. As pressure increases, typically due to the action of the user pressing the toothbrush against the teeth, the spring is compressed, which moves the moment arm until a threshold maximum pressure is reached, at which point the moment arm is moved to a position to operate a switch which results in a signal being directed to an indicator assembly which provides feedback to the user. The user then has the opportunity to change the pressure produced by his/her own action to a level below the threshold level. However, the known pressure sensors for toothbrushes are often complex and therefore expensive to implement, and in many cases do not provide reliable results. Hence, it is desirable to have a pressure-sensing mechanism which is compact, simple and relatively inexpensive, particularly for use in a resonantly driven power toothbrush.

SUMMARY OF THE INVENTION

Accordingly, the power toothbrush comprises: a handle portion containing a power drive system; a brushhead assembly, including a brushhead arm and a brush element at a distal end thereof; a drive train assembly responsive to a drive signal of the power drive assembly for producing a motion of the brushhead assembly; a magnet positioned so that it moves in accordance with the brushhead assembly motion, the magnet producing a magnetic field; a Hall effect sensor mounted within the magnetic field, wherein the magnetic field response has a phase shift relative to the phase of the drive signal; and a processor for determining the phase shift of the Hall sensor output due to load on the brush element during brushing operations and for producing a signal indicative of said load, in accordance with stored information in the appliance relating values of phase shift to load.

BEST MODE FOR CARRYING OUT THE INVENTION

Figure 1:
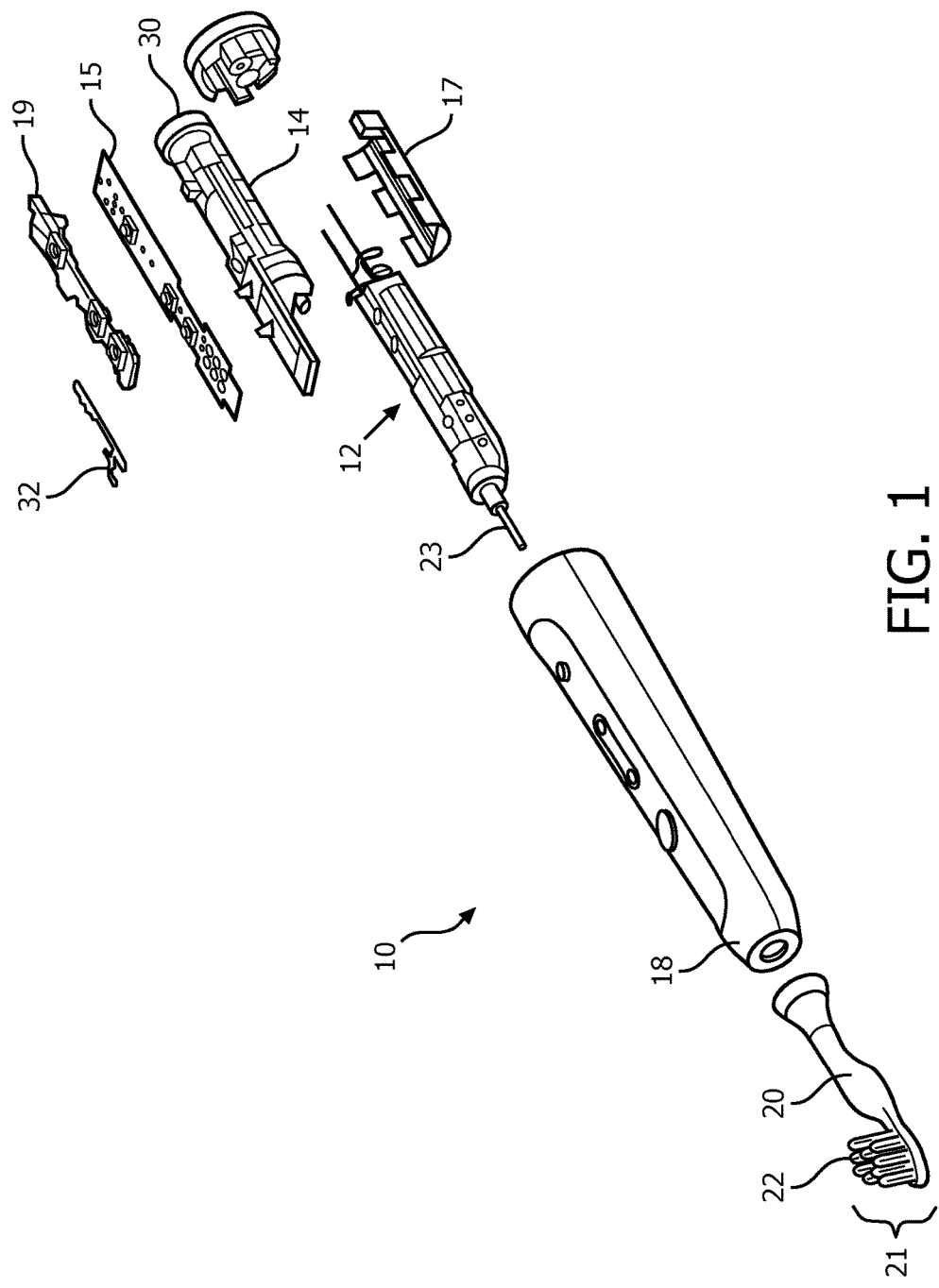
FIG. 1 is an isometric view of a portion of a power toothbrush which includes the pressure-sensing system disclosed herein.

FIG. 1 is an exploded view of a resonant drive power toothbrush which incorporates the pressure sensing mechanism described and shown below. The power toothbrush shown generally at 10 includes a drive train assembly 12 resonantly driven by a power system 14 which includes a battery and electronics carrier (PCB). The drive train and power assembly are both conventional power toothbrush elements and hence are not described in detail. The power toothbrush shown also includes a rubber bumper 17 which acts as a cushion for the drive train within a housing 18. The power toothbrush further includes a printed circuit board with a microprocessor control 15 for creating the drive signal for the power system. Removably secured to a drive stem 23 from the drive train is a brushhead assembly 20, at the distal end of which is a brush member 21, with a bristle field 22. At the rear end of the drive assembly is a magnet 30. In the embodiment shown, the magnet has the following dimensions: 13.4×9.0×4.0 (mm). One example of a suitable magnet is Neodymium. Mounted within the power toothbrush is a Hall effect sensor 32 positioned adjacent the magnet. An example of a suitable Hall effect sensor is an Allegro A1395, manufactured by Allegro Microsystems. The Hall effect sensor 32 can be mounted in various positions within the power toothbrush; but in one embodiment, the Hall sensor is mounted on a flex circuit 34, which is attached to the printed circuit board 15 so that the Hall sensor can respond to a changing magnetic field as the toothbrush moves in operation.

Figure 2:
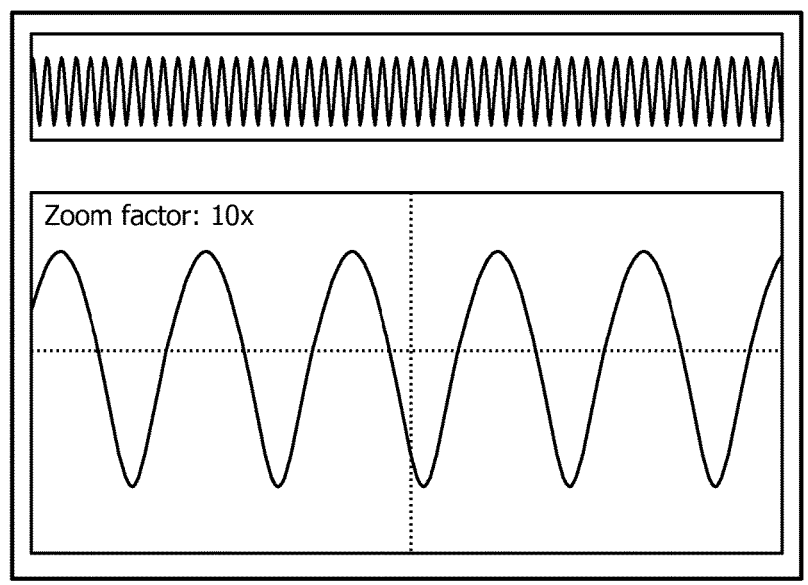
FIG. 2 is a typical output signal diagram from a Hall effect sensor portion of the present system.

Under no-load conditions, a sinusoidal output is produced from the Hall sensor, as shown in FIG. 2. In the present invention, the Hall sensor detects a change in phase between the drive signal for the appliance and the mechanical response of the drive train/brushhead assembly, as followed by movement of the magnet 30, as pressure on the bristle field changes. As pressure increases, the phase shift increases. Typically, the change in phase will be linear over a defined change of pressure (force), from 0 grams to at least 300 grams, at which point the pressure has exceeded a typical maximum value for comfort and effectiveness.

Information is stored in the processor 15 which specifically relates phase shift values to force applied, for the particular appliance being tested, so that a specific phase shift is accurately indicative of pressure/force applied to the bristle field of that toothbrush.

The drive signal is typically a square wave, which in one cycle rises from a zero level to a positive value and after a time determined by the drive frequency declines to a value of opposing polarity, which drive signal cycle continues for the duration of operation of the toothbrush for each event. In the embodiment shown, the drive frequency is 250 Hz, and the amplitude of motion is between 9-11°. This is, however, only one example of operation. The frequency and amplitude may be varied.

The toothbrush is initially calibrated to determine a time "t" offset which exists between the square wave motor drive signal and the mechanical response signal, as indicated by the signal output from the Hall sensor. This is done under no-load conditions, so that the static phase relationship between the motor drive signal and the response signal is known and can be in effect a zero set for signal processing during actual operation of the toothbrush.

Figure 3:
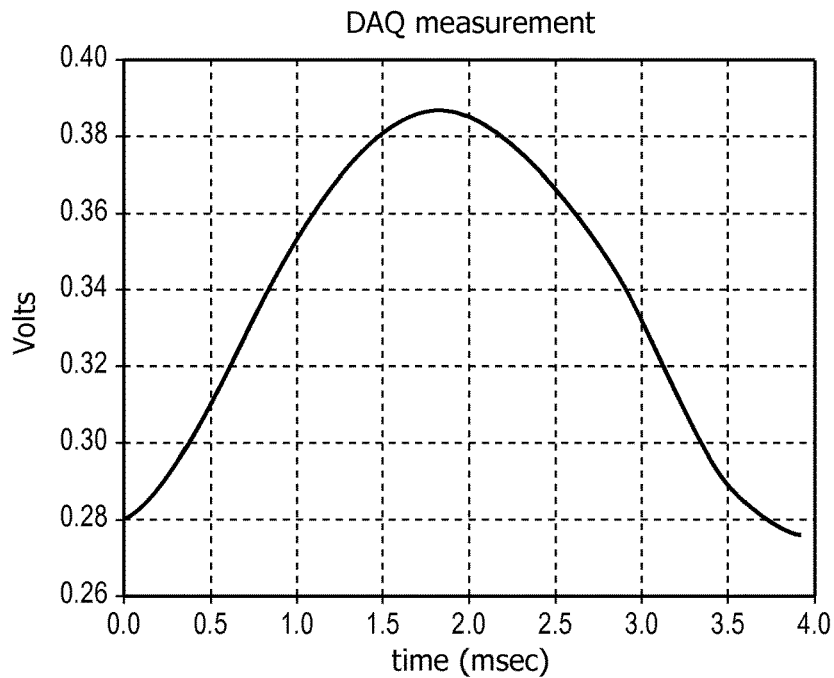
FIG. 3 is an output of a half cycle of a Hall effect sensor with an output signal calibrated to the drive signal for the appliance.
Figure 4:
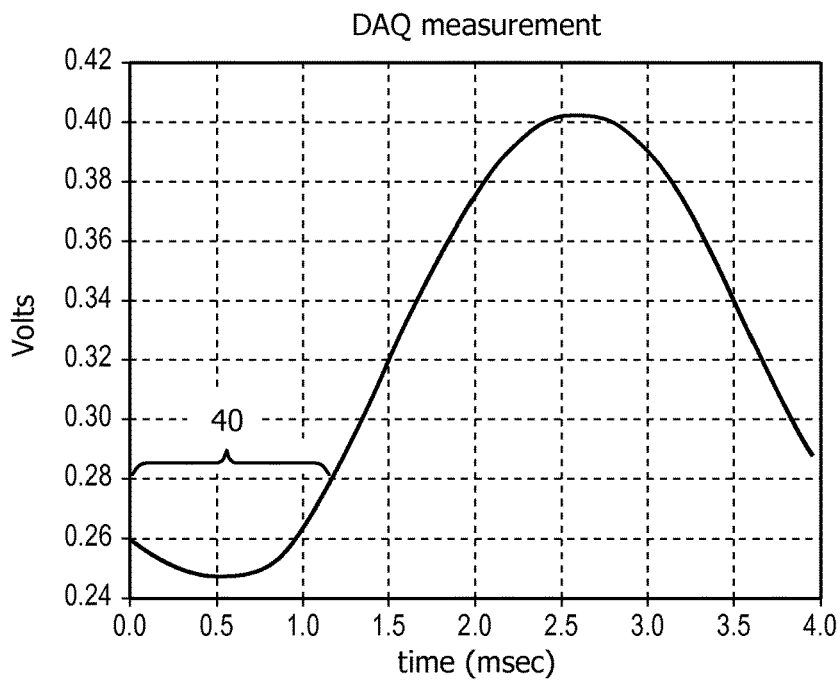
FIG. 4 is a diagram similar to that of FIG. 3 showing a phase shift in the output signal due to load.

FIG. 3 shows a single half-cycle of the response signal (Hall sensor output) with the left-hand edge of the signal synchronized to the rising edge of the motor drive signal. As pressure/load is applied to the bristle field, there will be a phase shift in the Hall sensor output signal relative to the motor drive signal. One example of a phase shift is illustrated in FIG. 4.

Figure 6:
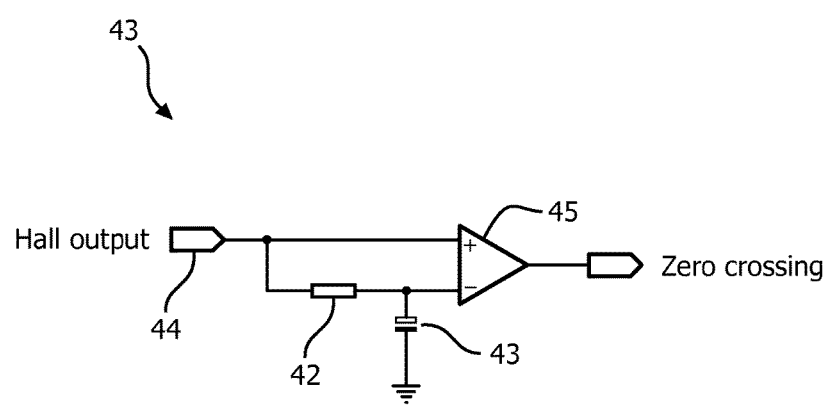
FIG. 6 is a diagram of a zero crossing circuit used in one embodiment of the invention.

The value of the phase shift is determined continuously as load is applied to the bristle field. There are many ways to determine phase shift. One is by determining zero crossing. As the phase shifts, the zero crossing of the response signal from the Hall sensor will shift in direct proportion. The zero threshold is determined by averaging the signal over a number of cycles. The time from the start of the motor drive cycle to the first transition of the sensor signal through this zero threshold is then measured. The zero crossing provides an indication of the phase shift. An example of a suitable zero crossing circuit is shown in FIG. 6. A resistor 42 and capacitor 43 form a low pass circuit to filter the AC signal 44 from the Hall sensor. The resulting average voltage is one input to a comparator 45. The other input to the comparator is the Hall sensor output directly. The output of the comparator 45 transitions as the Hall sensor AC signal passes through its average value.

Another possibility for obtaining phase shift information is by a quadrature sampling process, in which four samples are used per cycle to extract the DC offset and phase of a sine wave. Four samples are taken 90° apart, in the calculation below by $S_1$, $S_2$, and $S_4$. The average voltage, or the DC offset, can be calculated:

$$V_0 = \frac{S_1 + S_3}{2} = \frac{S_2 + S_4}{2}$$

The signals will typically include noise, so that multiple samples are typically averaged to smooth results. To calculate the phase, two samples of in-phase and quadrature phase are defined as follows:

$$I = \frac{S_1}{V_0} \text{ and } Q = \frac{S_2}{V_0}$$

with the phase angle being defined as:

$$\theta = \operatorname{atan2}\left(\frac{I}{Q}\right)$$

Averaging I and Q over multiple samples is effective to reduce noise.

The above are just two examples of determining phase shift. Other techniques can be used.

Figure 5:
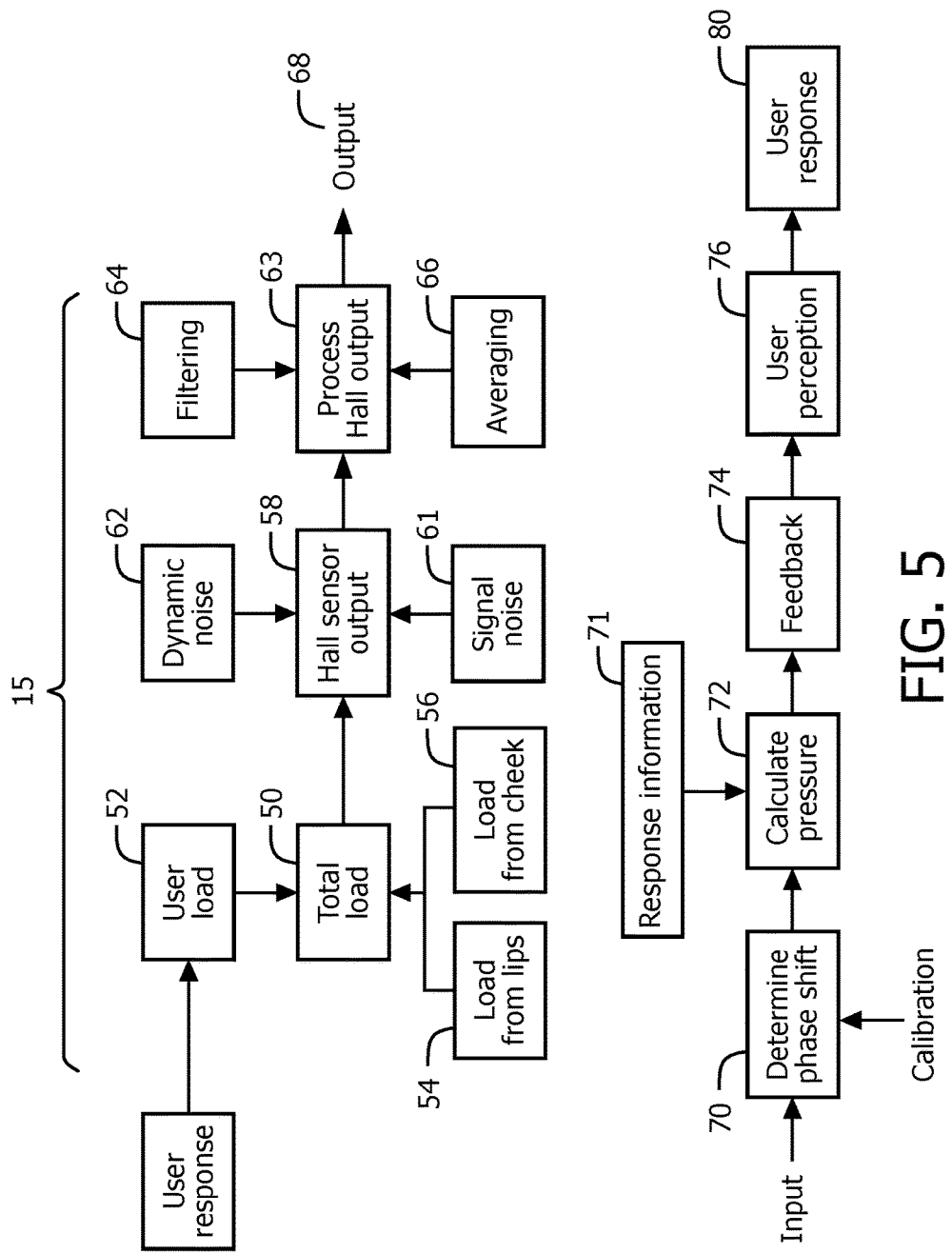
FIG. 5 is a diagram of the processor and its functions to determine the pressure applied to the bristle field during use of the toothbrush.

The overall processing sequence is shown in FIG. 5. The total load of pressure on the bristle field, referred to at 50, comprises generally the pressure applied directly by the user 52, as well as the load which occurs due to the lips 54 and the cheek 56 of the user during actual brushing.

The total load creates a phase shift between the motor drive signal and the Hall sensor output signal representing the response of the system. The Hall sensor output 60 is shown at 58. The sensor output signal is affected by signal noise 61, which can be from various sources, including from the Hall sensor itself, as well as variations in sensor mounting or a change in the resonant system over time. The Hall sensor output is also sensitive to dynamic noise 62, which typically is produced by the vibration from the drive train.

The Hall sensor output is then processed at 63, which can include filtering 64 and averaging 66 to produce as clean an output signal as possible. This is represented, for instance, by the signal in FIG. 4. This signal, represented as output 68 in FIG. 5, is then subject to further processing. The actual phase shift is determined at 70. As indicated above, this phase shift can be determined by a standard zero crossing circuit. The phase shift is determined for a calibrated appliance. The processor then uses the phase shift to calculate the actual pressure by use of a response curve or stored information 71 which relates phase shift along one axis to pressure along the other axis, at 72. Typically, as indicated above, the response curve is a straight line for phase shift against pressure, over at least a range of pressure (force) of 0-300 grams.

The result, which is provided continuously, is used to produce a feedback signal, which can be auditory, visual or sensory, represented at 74. The feedback can indicate one or more of the following: (1) the pressure has exceeded a maximum pressure threshold; (2) the pressure has not reached a minimum pressure; and (3) the pressure is between the minimum and maximum pressure thresholds, which is acceptable. The feedback is perceptible to the user, as represented by block 76, which is intended to result in a user response, represented by block 80. A user response will typically result in a changed user load, with a resulting change in the value of determined pressure. The information will be provided to the user on a continuous basis, so that the user can maintain the load of the bristle field between the maximum and minimum thresholds, for effective and safe operation.

Accordingly, a power toothbrush has been disclosed which includes a pressure-sensing system which uses a Hall effect sensor and a determination of a phase shift due to pressure, wherein information stored in the appliance relates values of phase shift to pressure. The disclosed system is relatively simple and inexpensive, as well as being reliable.

Although a preferred embodiment of the invention has been disclosed for purposes of illustration, it should be understood that various changes, modifications and substitutions may be incorporated in the embodiment without departing from the spirit of the invention, which is defined by the claims which follow.

What is claimed is:
1. A power toothbrush, comprising:
a handle portion containing a power system;
a brushhead assembly, including a brush member having a bristle field at a distal end thereof;
a drive train assembly responsive to a drive signal of the power system and configured to produce a motion of the brushhead assembly;

a magnet secured to the drive train and positioned to move in conjunction with the brushhead assembly motion, the magnet producing a magnetic field;

a Hall effect sensor mounted within the handle portion and positioned adjacent the magnet, wherein the Hall effect sensor is configured to detect a change in phase between the drive signal of the power system and the motion of the brushhead assembly as pressure on the bristle field changes as applied to teeth of a user during operation under load conditions; and wherein the Hall effect sensor is further configured to respond with a phase shift in a Hall effect sensor output signal relative to the phase of the drive signal; and a microprocessor control configured to determine a value of the phase shift of the Hall effect sensor output due to pressure on the bristle field during brushing operations and further configured to produce a feedback signal indicative of said pressure by using stored information in the power toothbrush relating values of phase shift pressure.

2. The power toothbrush of claim 1, wherein the processor is calibrated such that the Hall effect sensor output signal is coincident in phase with the drive signal under no-load conditions.

3. The power toothbrush of claim 1, including a zero crossing circuit for determining the phase shift.

4. The power toothbrush of claim 1, wherein the microprocessor control includes the capability of averaging the signal output of the Hall effect sensor over several cycles and for filtering noise from the Hall effect sensor signal output.

5. The power toothbrush of claim 1, wherein the microprocessor control uses the stored information to correlate the output of the Hall effect sensor with a first pre-established threshold and to provide feedback information to the user when pressure on the brush member exceeds the first threshold value.

6. The power toothbrush of claim 5, wherein the first threshold value represents a maximum pressure value.

7. The power toothbrush of claim 5, including a second pre-established threshold representing a minimum pressure value.

8. The power toothbrush of claim 1, wherein the output signal from the Hall effect sensor is continuous and the feedback signal from the microprocessor is also continuous, representing a continuous indication of pressure on the brush member.

9. The power toothbrush of claim 1, wherein the feedback information is in a form recognizable by the user.

10. The power toothbrush of claim 1, wherein the phase shift under load conditions is determined through quadrature sampling.

* * * * *